(12) United States Patent
Eckhardt et al.

(10) Patent No.: US 8,675,194 B2
(45) Date of Patent: Mar. 18, 2014

(54) APPARATUS FOR MEASURING THE RETROREFLECTANCE OF MATERIALS

(75) Inventors: Stephen K. Eckhardt, White Bear Lake, MN (US); Norbert L. Johnson, St. Paul, MN (US)

(73) Assignee: Gamma Scientific Inc., San Diego, CA (US)

( * ) Notice: Subject to any disclaimer, the term of this patent is extended or adjusted under 35 U.S.C. 154(b) by 5 days.

(21) Appl. No.: 13/106,576

(22) Filed: May 12, 2011

(65) Prior Publication Data

US 2012/0287432 A1 Nov. 15, 2012

(51) Int. Cl.
*G01J 3/28* (2006.01)

(52) U.S. Cl.
USPC ........................................... 356/326

(58) Field of Classification Search
USPC .................. 356/326, 328, 334, 445
See application file for complete search history.

(56) References Cited

U.S. PATENT DOCUMENTS

| | | | |
|---|---|---|---|
| 3,414,355 A | 12/1968 | Fastie et al. | |
| 4,171,910 A | 10/1979 | Derderian et al. | |
| 4,368,982 A | 1/1983 | Van Arnam et al. | |
| 4,831,276 A * | 5/1989 | Hyakumura | 250/559.09 |
| 5,734,501 A | 3/1998 | Smith | |
| 6,193,401 B1 * | 2/2001 | Girkin et al. | 362/551 |
| 7,298,487 B2 | 11/2007 | Hansen et al. | |
| 7,961,328 B2 | 6/2011 | Austin et al. | |
| 2008/0170225 A1 * | 7/2008 | de Boer et al. | 356/327 |
| 2010/0020320 A1 * | 1/2010 | Yao | 356/319 |

* cited by examiner

*Primary Examiner* — Tarifur Chowdhury
*Assistant Examiner* — Abdullahi Nur
(74) *Attorney, Agent, or Firm* — Christie, Parker & Hale, LLP (57) ABSTRACT

The present invention comprises various embodiments of a retroreflectometer capable of measuring the retroreflectance of a material. The retroreflectometer comprises an illumination path and a retroreflection path. The illumination path comprises focusing optics, a source aperture, a beamsplitter and a collimating lens. The retroreflection path comprises a focusing lens, a beamsplitter, a receiver aperture and a receiver. The source aperture shapes the transverse profile of the light to make it appropriate to the measurement. Focusing optics, such as a biconvex lens, may be placed between the light source and the source aperture. After the beam is reflected by the object under test, it enters the retroreflection path of the instrument. The focusing lens focuses the light through the beamsplitter and onto the receiver aperture. The receiver aperture may be the input slit for a spectrometer, or there may be optics, such as a lens or an optical fiber, that transfer the light from the aperture to the receiver. A photopically corrected detector, multiple detectors with filters or a spectrometer may be used in various embodiments of the present invention as the receiver.

6 Claims, 6 Drawing Sheets

APPARATUS FOR MEASURING THE RETROREFLECTANCE OF MATERIALS

BACKGROUND OF THE INVENTION

1. Field of the Invention

The present idea relates in general to the field of retroreflected light and more particularly to an apparatus used to measure retroreflected light.

2. Description of the Related Art

Retroreflectance is the ability of an object or material to return light in the direction from which it came. This direction is defined by a narrow cone with its point on the object under test and opening toward the source, with a cone angle of less than a degree. Most materials retroreflect at least a small amount of light. For instance, white paint reflects (scatters) light in all directions, so some of the light must go back toward the light source. The amount of light retroreflected by white paint however is small because the light is almost uniformly scattered into a hemisphere (i.e. white paint is roughly Lambertian) so a cone with an angle of less than a degree would contain very little of the reflected light. A mirror is an example of an object that does not retroreflect, except when the light is normally incident. For all other angles of incidence, the light is reflected in a direction that has the same angle to the normal to the mirror surface but on the opposite side of the normal. A cube corner is a common example of a retroreflector; it retroreflects almost all of the light incident on it, although the return beam tends to be slightly displaced from the incident beam. A second example of a retroreflector is a glass sphere with a refractive index of 2.0, the back side of which is coated with a reflective material such as silver or aluminum.

Objects that exhibit retroreflectance are known in the art, and are commonly used in road signs. For example, U.S. Pat. No. 5,734,501, the disclosure of which is hereby incorporated herein by reference in its entirety, discloses a "Highly Canted Retroreflective Cube Corner Article."

Further, ASTM International has a series of standards for measuring retroreflectance of materials used for road signs. These include D 4956 "Standard Specification for Retroreflective Sheeting for Traffic Control", E 808 "Practice for Describing Retroreflection", E 809 "Standard Practice for Measuring Photometric Characteristics of Retroreflectors", E 810 "Test Method for Coefficient of Retroreflection of Retroreflective Sheeting Utilizing the Coplanar Geometry", E 811 "Practice for Measuring Colorimetric Characteristics of Retroreflectors Under Nighttime Conditions", E 1709 "Standard Test Method for Measurement of Retroreflective Signs Using a Portable Retroreflectometer at a 0.2 Degree Observation Angle" and E 2540 "Standard Test Method for Measurement of Retroreflective Signs Using a Portable Retroreflectometer at a 0.5 Degree Observation Angle", the full disclosures of each of which are hereby incorporated herein by reference. These standards describe test methods and practices used for measuring retroreflective materials, but they do not completely specify the instruments used for performing the measurements. For example, E 811, Section 8.4 specifies a Light Projector Source that conforms to CIE Standard Source A (which is further defined in Section 3.2.5 as a "gas-filled tungsten-filament lamp operated at a correlated color temperature of 2855.6K) that produces a uniform patch of light on the sample and has either an adjustable iris diaphragm or a selection of fixed apertures. This leaves considerable discretion to the designer of the instrument regarding how to make the light patch uniform and obtain sufficient brightness on the sample.

Instruments for measuring retroreflectivity, sometimes referred to as retroreflectometers, are known in the art. Two broad categories of such instruments are those that include a beamsplitter, for example U.S. Pat. No. 4,368,982, the disclosure of which is hereby incorporated in its entirety by reference, and those that do not, for example U.S. Pat. No. 7,298,487, the disclosure of which is also hereby incorporated by reference in its entirety. In the latter case, the light source and the receiver are slightly displaced so that they do not occupy the same space. However, the relevant ASTM standards require that the angular separation of source and receiver be less than a degree, so the apparatus is inherently large due to the physical size of available light sources and receivers.

Retroreflectometers that include a beamsplitter work as follows. Light from a light source is reflected by the beamsplitter in the direction of the object under test. A portion of the light is also transmitted by the beamsplitter, but it is not relevant to the measurement and will be ignored. The reflected light impinges on the object and is, to some extent, retroreflected. The retroreflected light passes through the beamsplitter (again ignoring the irrelevant light) and is incident on the receiver. Because of the presence of the beamsplitter, the light source and receiver, although physically separated, may be optically coincident. This enables an apparatus that is more compact than one that does not have a beamsplitter. The tradeoff for use of a beamsplitter is that roughly three fourths of the light is lost.

One problem with the prior art instruments is that they either depend on a laser for illumination, see, e.g., U.S. Pat. No. 4,171,910, and thus measure retroreflectance at only one wavelength, or they depend on color filtration of the light. The two principle types of color filtration are photopic, as described in ASTM E 809-08, Section 8.2.1, and tristimulus, as described in ASTM E 811, Section 8.2.1. Photopic color filtration is intended to enable correction of the wavelength sensitivity of detectors that do not have a spectral response curve that mimics the human eye, thereby resulting in an electronic output that simulates the eye. Photopic filtration of detectors is difficult due to the significant difference between the spectral response curve of detectors and that of the human eye and because there are slight but significant variations from one detector to the next, even of the same type.

Tristimulus color filtration is used in instruments designed to measure color as well as optical power. Three filters and three detectors, which may be physically combined into one unit, are required. In general, one detector provides an electronic signal corresponding to blue input, one to green and one to red. The difficulty in creating accurate tristimulus filters that cause detectors to respond appropriately to light of different wavelengths is similar to the difficulty of creating an accurate photopic filter.

A second problem with the prior art instruments is that they assume that the distribution of retroreflected light is generally rotationally symmetric. In ASTM E 808-01, Section 6.1.2 and FIG. 5, an Intrinsic System of geometry is described, in which the receiver is positioned at an angle of gamma about the illumination axis to make a measurement. Unless gamma is variable in an instrument and a series of measurements is taken, a lack of symmetry in the distribution of the retroreflected light could produce a measurement error. This was not a significant problem with the older materials based on spherical glass beads, but the newer prismatic materials can create measurably asymmetric distributions. To circumvent this difficulty, ASTM E 1709 and E 2540 mention the use of a receiver that has an annular opening. While this allows simultaneous measurement of all values of gamma, it poses difficulties in the design of the receiver.

The present invention overcomes, inter alia, these difficulties.

BRIEF SUMMARY OF THE INVENTION

The present invention comprises various embodiments of a retroreflectometer capable of measuring the retroreflectance of a material. The retroreflectometer comprises an illumination path and a retroreflection path. The illumination path comprises a light source, a source aperture, a beamsplitter and a collimating lens. The retroreflection path comprises the collimating lens, the beamsplitter, a receiver aperture and a receiver. The light source may be anything that emits visible electromagnetic radiation, such as, but not limited to, an incandescent lamp or a light emitting diode (LED). The source aperture shapes the transverse profile of the light to make it appropriate to the measurement. It may be circular in shape or annular, as appropriate. In some embodiments, focusing optics, such as a biconvex lens, may be placed between the light source and the source aperture. When present, the focusing optics increase the amount of light that passes through the source aperture and restrict the angular extent of the beam of light. The beamsplitter reflects substantially half of the incident light and transmits the remaining half, although some light may also be absorbed, decreasing the reflectance and transmittance. By definition, the collimating lens accepts the divergent beam from the source aperture and converts it to a generally parallel beam that is incident on the object under test. After the beam is reflected by the object under test, it enters the retroreflection path of the instrument. The collimating lens then focuses the light through the beamsplitter and onto the receiver aperture. The receiver aperture may be the input aperture for the receiver, or there may be optics, such as a lens or an optical fiber, that transfer the light from the aperture to the receiver. A photopically corrected detector, multiple detectors with filters or a spectrometer may be used in various embodiments of the present invention as the receiver. If a spectrometer is used, it splits the light into its component wavelengths and converts the light into an electrical signal that is proportional to the amount of light in each waveband. Inclusion of the spectrometer in various embodiments of the present invention avoids the problems inherent in photopic correction of a detector, and provides more information than tristimulus filters can.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION

With reference now to the Figures, the present invention will be described. Specifically in FIGS. 1-3, one embodiment 100 of a system, apparatus and method of the present invention is illustrated as comprising a light source 101, a first optical path, also referred to herein as the illumination optical path 200 and a second optical path, also referred to herein as the retroreflected optical path 300 comprising a receiver 108 and optional relay optics 107.

Figure 1:
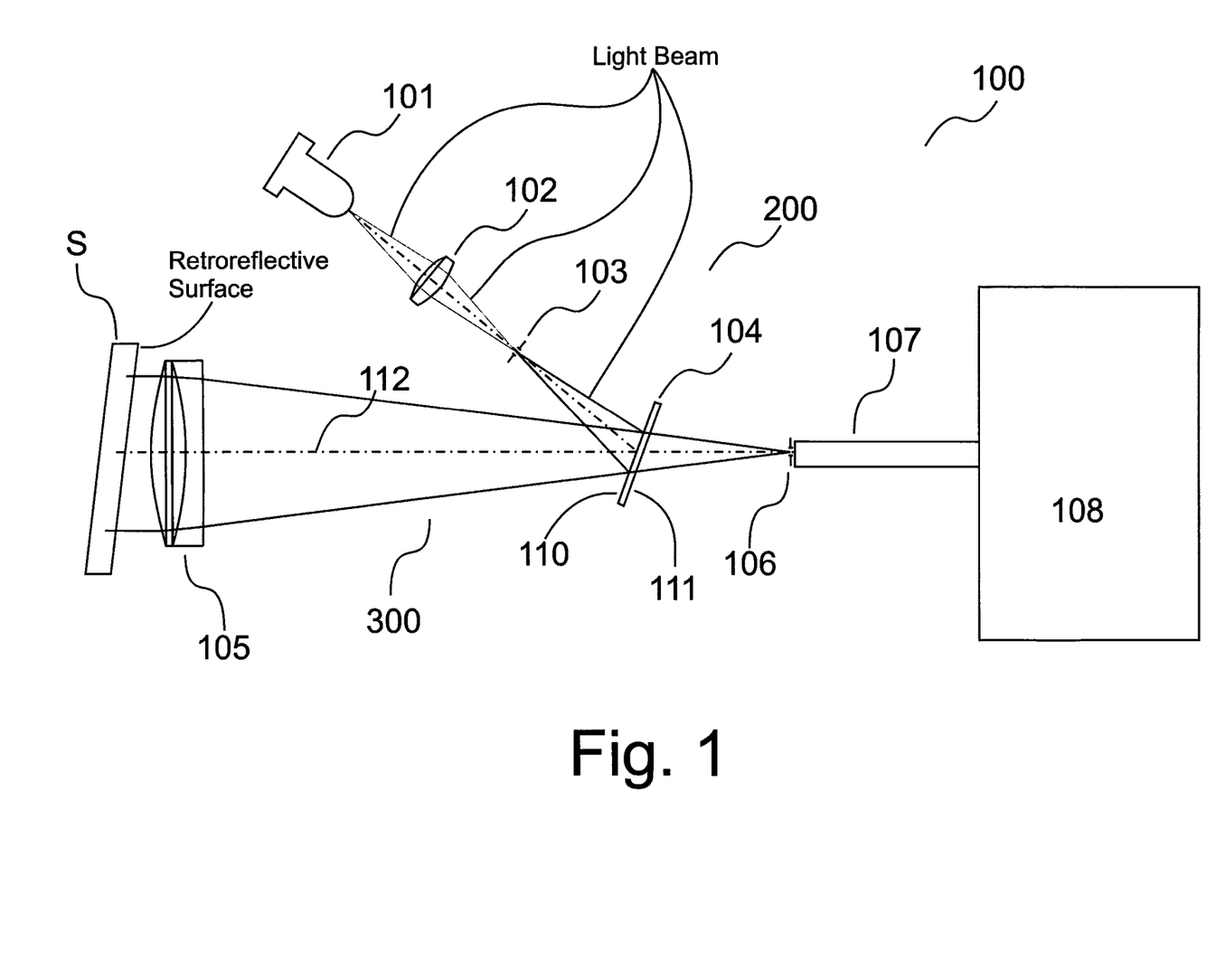
FIG. 1. is a side view of one embodiment of a system and apparatus of the present invention.
Figure 2:
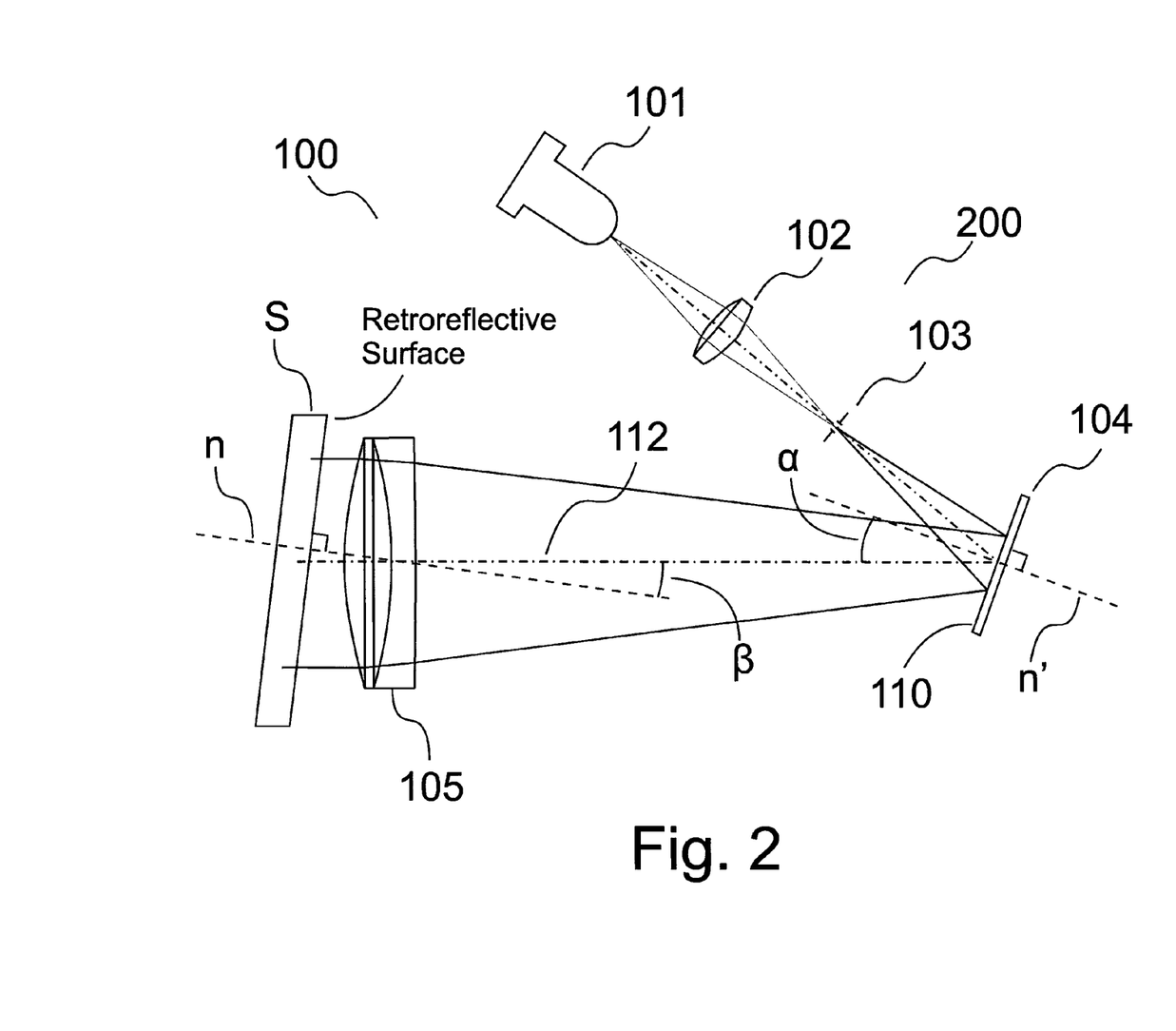
FIG. 2. is a schematic drawing showing the illumination optical path of one embodiment of a system and apparatus of the present invention.

The first optical path or illumination optical path, 200 is illustrated in FIGS. 1 and 2. Light is emitted by a light source 101 which may be an LED, an incandescent lamp or some other type of light emitting device. If the color were being measured by tristimulus filters, it would be important to use an incandescent lamp operated at a specific correlated color temperature or other light source that produces a smooth spectrum, so that variability in the light source would not necessitate careful matching of the filters to the light source in order to produce consistent readings. An incandescent lamp is specified in ASTM E811, Section 8.4. This standard also mentions the use of a "telespectroradiometer" in Section 11.3 and teaches that use of such an instrument, rather than the "telecolorimeter," which uses tristimulus filters to measure color, "does not require that the source be at the proper color temperature." However, it does not negate the requirement of an incandescent lamp in Section 8.4.

Next in the illumination optical path 200 is the optional focusing optics, i.e. a relay lens 102. Inclusion of a relay lens 102 is preferable due to increased efficiency and decreased stray light, but it is not mandatory for all embodiments of the present invention. The relay lens 102 refocuses the light from the light source onto the source aperture 103. To optimally execute this refocusing function, the present invention must meet several constraints. The first constraint is that the source aperture 103 must be substantially uniformly illuminated. One way of doing this is to assure that the light source is not imaged exactly on the aperture 103 but either before or after it. However, care must be taken to assure that the light is not so far out of focus that insufficient light passes through the aperture 103. For this reason, the focal spot should be a few times the diameter of the aperture 103. Another constraint is that the f-number of the light beam produced by the relay lens 102 should match that of the collimating lens 105. This is important because if the collimating lens 105 is under-filled, a smaller than desired sample size will result, but if it is overfilled, more stray light will be scattered within the instrument, with the possible result of inaccurate measurements. Relay lens 102 may comprise, e.g., a biconvex lens, though other alternative lenses may be utilized as will be readily apparent to the skilled artisan.

As mentioned above, the source aperture 103 is the next component in the illumination optical path 200. Source (and receiver) apertures 103, 106 are described in ASTM E 808-01, Section 9. Both circular and rectangular apertures are mentioned, although rotational symmetry is discussed in ASTM E 809-08, Section 3.2.8.1 and only circular apertures are mentioned in Section 9.1. According to ASTM Standard E810-03, a circular aperture for source and receiver apertures 103, 106, such as is illustrated in FIG. 4 should be used.

Figure 4:
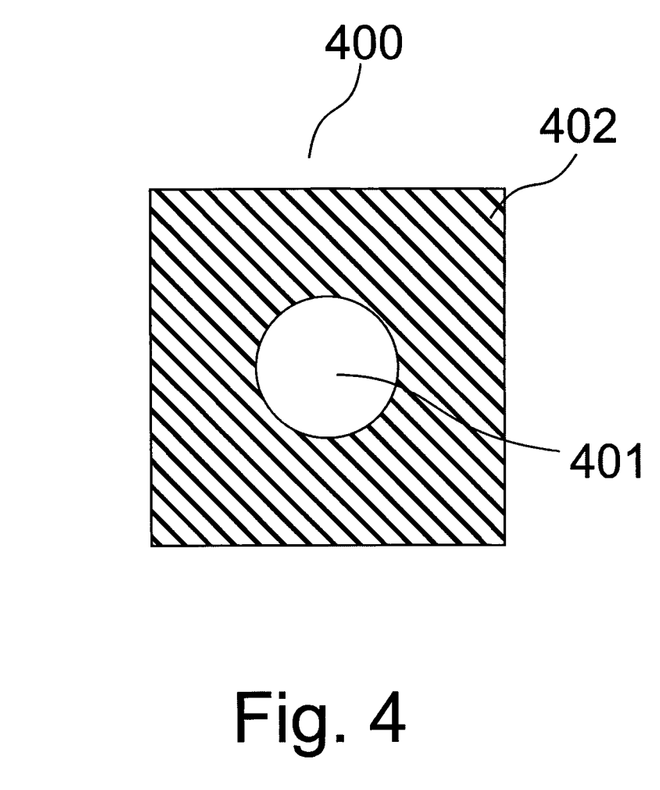
FIG. 4. is a schematic drawing showing a circular source aperture.

Thus, a circular aperture comprising source and receiver apertures 103, 106 in various embodiments of the present invention is illustrated in FIG. 4. One exemplary circular aperture for source and receiver apertures 103, 106 may subtend an angle of 0.167° would have a diameter of 0.29 mm and an area of 0.066 mm².

Circular apertures 400 can be made either as a hole in an opaque material, such as metal, or as a clear area on the surface of a piece of glass that is otherwise coated with an opaque material, such as black chrome. A variable circular aperture, known as an iris, could also be used.

Figure 3:
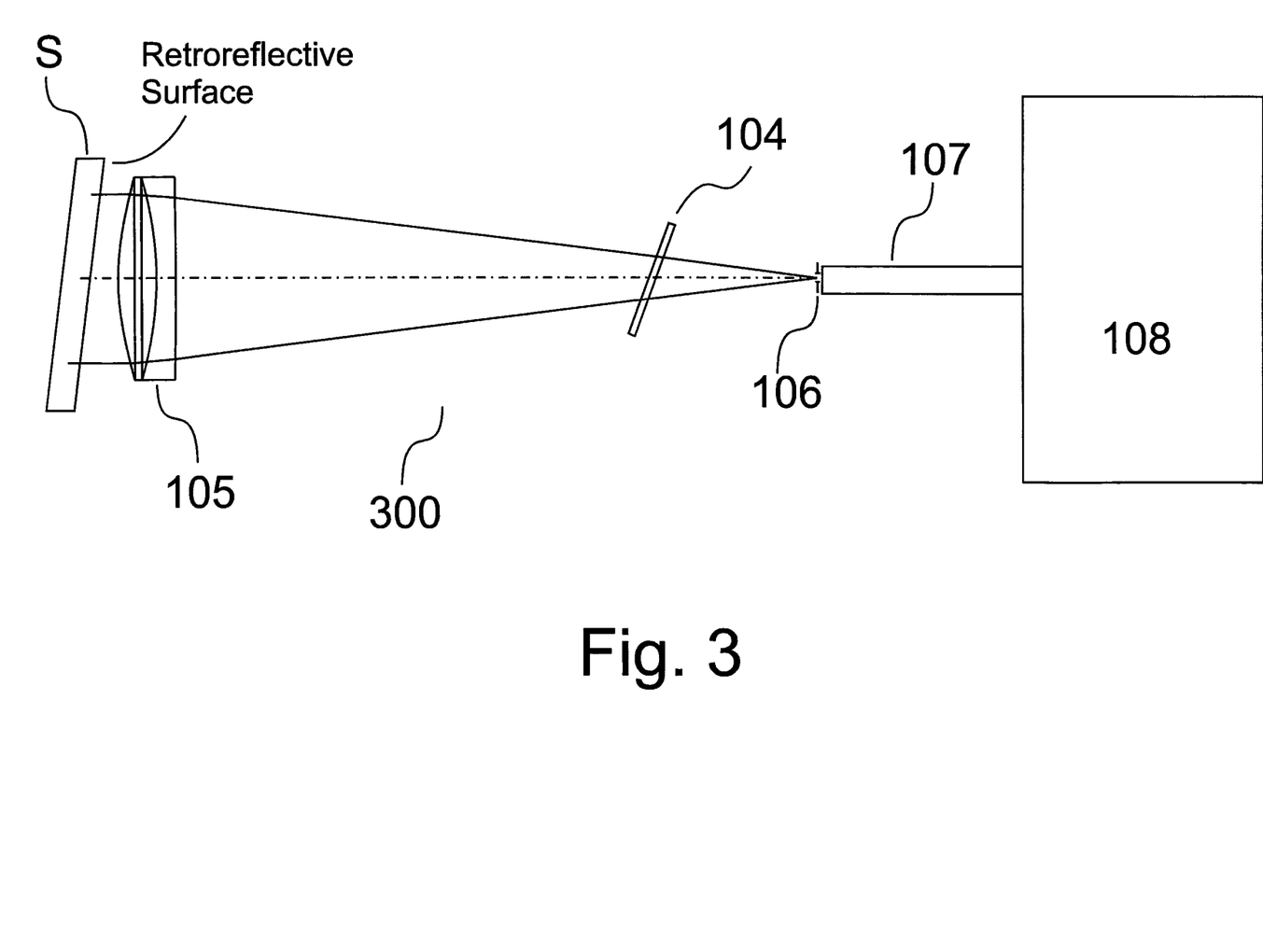
FIG. 3. is a schematic drawing showing the retroreflected optical path of one embodiment of a system and apparatus of the present invention.

Note that in practice the hatched area 402 would be opaque. To meet the ASTM D4956-09 standard, the opening 401 must be circular and subtend an angle of 0.167° as seen from the collimating lens 105 as illustrated in FIGS. 1-3. ASTM 1709 and 2540 describe an "annular instrument", but both of these standards specify that the source aperture is to be circular; only the receiver aperture may be annular.

Figure 5:
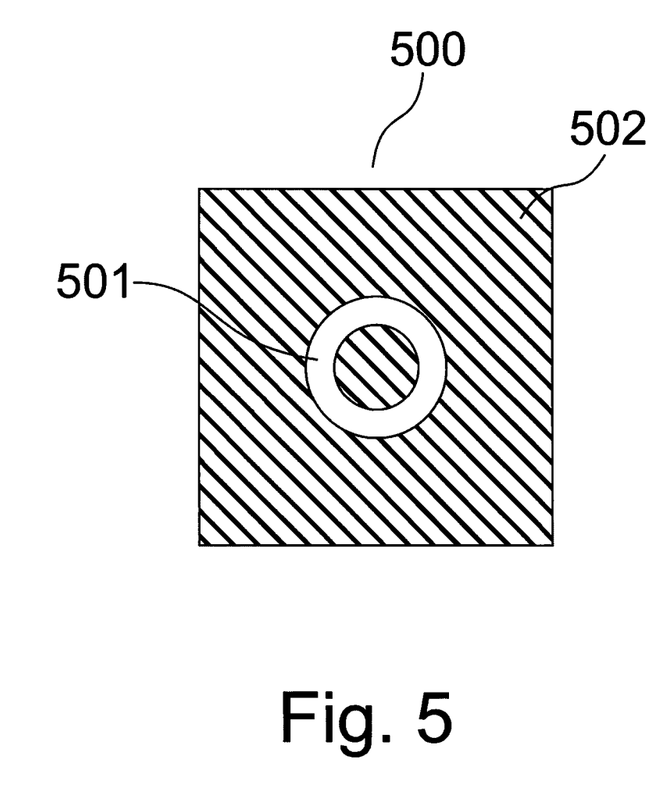
FIG. 5. is a schematic drawing showing an annular source aperture.

The general shape of an annular aperture 500 is shown in FIG. 5. The hatched areas 502 would be opaque in practice. One embodiment of the aperture 500 may consist of an annulus 501 with an inner angular subtense of 0.25° and an outer one of 0.417° as seen from the collimating lens as is well understood by the skilled artisan. For example, if the collimating lens has a focal length of 100 mm, the inner diameter of the annulus would be 0.436 mm and the outer diameter would be 0.727 mm, so the area of the annulus would be 0.266 mm². Annular apertures are preferably made of coated and patterned glass, although other means of fabrication are possible as will be readily understood by those skilled in the art. Other embodiments of aperture 500 will readily present themselves to the skilled artisan; each such embodiment is within the scope of the present invention.

Thus, the invention 100 described herein may include an annular source aperture 103, see FIG. 5, and a circular receiver aperture 106 or, alternatively, circular source and receiver apertures 103, 106 may be used.

The advantage of using an annular aperture such as illustrated in FIG. 5 on the source aperture 103 and a circular aperture as illustrated in FIG. 4 on the receiver aperture 106 is threefold. First, the use of an annular aperture overcomes the variation in measurements when the angle gamma, the orientation of the receiver about the optical axis, is changed. Second, most light sources are significantly larger than either aperture, 103, 106 while detectors are available in various sizes, so using an annular source aperture 103, with its greater area, increases the efficiency of the system. Third, the circular receiver aperture 106 embodiment is especially advantageous when a spectrometer is used as a receiver 108, because a smaller entrance (receiver) aperture 106 on a spectrometer leads to higher wavelength resolution if the size of the spectrometer is held constant.

The next optical element in the first optical path or illumination optical path 200 is a beamsplitter 104. Its function is to reflect substantially half of the light from the source aperture 103 to the collimating lens 105. Although a cube beamsplitter could be used, a simpler plate beamsplitter is sufficient as will be readily understood by the skilled artisan. The reflecting side 110 and the transmitting side 111 must both be optically flat, i.e., planar, to avoid inducing optical aberrations to the beam, with the reflecting side 110 closest to the light source 101 and the transmitting side 111 closest to the source aperture 106. A 50/50 split between reflection and transmission of the light by the beamsplitter 104 is preferable for maximizing system efficiency, although other ratios will work. The light that is transmitted from the illumination optical path 200 is of no further use, and may be absorbed by any suitable means.

Light that is reflected by the beamsplitter 104 will be collimated by the collimating lens 105. This lens 105 is shown as a cemented doublet, although any other suitable lens may be employed as the skilled artisan will readily understand; each such equivalent lens 105 is within the scope of the present invention. Upon leaving the collimating lens 105, the light will be incident on the sample S under test at entrance angle β, defined as the angle between the normal n to the reflective surface of sample S and the optical axis 112 of the collimating lens 105. Entrance angle β is defined in ASTM E 808 section 3.2.11 and is illustrated in FIG. 2. A preferred entrance angle β in various embodiments is 5 degrees, see, e.g., Section 7.12 of ASTM D 4956. Obviously, other entrance angle β selections may be made which are lesser than or greater than the preferred 5 degrees; each of these entrance angle selections are within the scope of the present invention. Moreover, the skilled artisan will readily appreciate that sample S may be any material whatever and is not a part of this invention.

Thus, embodiments of the first optical or illumination optical path 200 comprise a light source 101, the optional relay lens 102, the source aperture 103, the beamsplitter 104, specifically the reflective side 110 of beamsplitter 104, and the collimating lens 105.

The second optical path, also known as the retroreflection optical path 300 is shown schematically in FIGS. 1 and 3. Light that is reflected, scattered or retroreflected by the sample S enters the retroreflection optical path 300 through the collimating lens 105 which focuses the retroreflected light on a path directed toward the receiver aperture 106.

Since the collimating lens 105 focuses the portion of the entering light that is approximately collimated into the receiver aperture 106, it is desirable, though not necessary in various embodiments of the present invention, that the lens 105 be achromatic to assure that light of different wavelengths travels very nearly the same path and comes to a sharp focus. Specifically, to meet the requirements of ASTM E811 or ASTM E809, the light must be focused through an aperture, either circular as in FIG. 4 or annular as in FIG. 5, that has an angular subtense of 10 arc minutes.

In the preferred embodiment, the collimating lens 105 has a focal length of 100 millimeters, so the receiver aperture 106 has a diameter of 0.29 millimeters. The polychromatic root mean square (rms) spot radius produced by the lens 105 should preferably be no more than 10% of this diameter in order to assure that the aberrations of the lens do not affect the color measured by the instrument. A prescription for a lens 105 that meets these criteria is provided below in Table 1:

TABLE 1

| Radius | Thickness | Glass | Diameter |
|---|---|---|---|
| 48.19 | 5.6 | H-ZK14 | 30 |
| −53.00 | 3.0 | H-ZLAF56A | 30 |
| −687.318 | to focus | air | 30 |

(The glasses in Table 1 are available from CDGM Glass Company, USA, Rochester, NY.)

Light that has been focused by the collimating lens 105 next encounters the beamsplitter 104. Roughly half the light is reflected and half transmitted, as before. The half that is reflected comes to a focus in the vicinity of the source aperture 103, and has no effect on the measurement. Only light transmitted by the beamsplitter 104 will be measured by the receiver 108, therefore the light that is reflected can be absorbed by known means and is of no further consequence to the measurement of retroreflectance.

Because the transmitted light must come to a sharp focus before encountering the receiver aperture 106, there are several additional constraints on the beamsplitter 104. The first is, as discussed briefly above, that both the reflective side 110 and the transmitting side 111 of the beamsplitter 104 must be optically flat. It is not difficult to achieve the required flatness because the beam diameter is under a centimeter for various embodiments of the present invention, though other beam diameters greater than a centimeter are achievable and therefore within the scope of the present invention, and because the spot size is significantly larger than the diffraction limit. For these reasons, normal float glass, with surface flatness of 6 to 12 waves per inch is acceptably flat for the preferred embodiment. In other embodiments, in which the beam diameter on the beamsplitter is of the order of a centimeter or larger, flatter glass would be preferable.

The tilt of the beamsplitter 104 with respect to the optical axis 112 of the focusing lens 105 is also of some importance. Thus, the beamsplitter tilt angle is defined as being the angle $\alpha$ between the normal n' to the reflective face 110 of the beamsplitter 104 and the optical axis 112 of the collimating lens 105. Although angles as large as 45 degrees might be tolerable, converging light passing through a plane-parallel plate of glass, such as a beamsplitter 104, suffers from linear astigmatism. This astigmatism increases the spot size, so it should be minimized. There are two ways to minimize it. First, the beamsplitter 104 should be as thin as practical. A pellicle could be used if it is sufficiently strong, or a piece of glass with a thickness of less than approximately 2 millimeters. Second, the beamsplitter tilt angle $\alpha$ can be minimized. In the preferred embodiment, the tilt angle $\alpha$ is 20 degrees and the beamsplitter 104 thickness, i.e., the distance between sides 110 and 111 as illustrated, is 1 millimeter, although larger or smaller values could be used for either dimension.

After passing through the beamsplitter 104, the light is incident on the receiver aperture 106. As mentioned above, this aperture should be a circle, as shown in FIG. 4, and must subtend an angle of 10 minutes of arc, as seen from the focusing lens. Also as mentioned in the discussion of the source aperture 103, this aperture may be made of either coated and patterned glass or as a hole in metal or some other opaque material.

Several options exist for what comes next in the retroreflection path 300. One option is that the source aperture 106 be the entrance aperture for the receiver. If the receiver is a spectrometer and the size of the aperture and the focal length of the spectrometer's collimating mirror (or lens) are such that the spectral resolution is sufficient for the purpose, this will work and will be the simplest solution. Alternatively, the light may be passed from the source aperture 106 to the receiver 108 by a receiver relay lens (not shown) or an optical fiber 107.

A receiver relay lens may be a single lens, an achromatic doublet, a triplet, a pair of achromatic doublets or any other suitable lens. One advantage of using a lens is that it can change the f-number of the beam to match the entrance f-number of the spectrometer, if one is used. Another advantage is that it could be used to correct residual aberrations of the collimating lens 105.

Transferring the light from the receiver aperture 106 to the receiver 108 may also be accomplished by an optical fiber 107. This can be advantageous because it allows flexibility in the position of the receiver 108, which may be adjacent to the receiver aperture 106 or may be several meters away. An optical fiber also scrambles the light from the receiver aperture 106, so that the receiver 108 is uniformly illuminated. Uniform illumination, especially with regard to well mixed colors, is important for an instrument designed to measure color. It is also helpful in embodiments including a spectrometer with an entrance slit that is tall and narrow and not well matched to the circular aperture, as is common.

The receiver 108 is the final component in the second, or retroreflection, optical path. Its job is to convert the light into an electrical signal that contains information about the amount and color of the incident light. To this end, the receiver 108 may be multiple photodetectors, such as silicon photodiodes, with appropriate filters, a single photodetector with a photopic filter or a spectrometer.

Thus, the second, or retroreflection, optical path comprises the collimating lens 105, the beamsplitter 104, the receiver aperture 106, an optional means for transferring light from the receiver aperture 106 to the receiver 108, such as an optical fiber 107 and receiver 108.

Receiver 108 may, in certain embodiments, comprise a spectrometer. Spectrometers are well known in the art. Their function is to split or separate the light into its various wavelengths so that the relative power across the color spectrum can be measured by an array detector, such as photodiode array or a CCD. Color can, under certain conditions, be determined by measuring the power in as few as three wavelength bands, so high spectral resolution is not required. The visible spectrum consists of electromagnetic radiation between wavelengths of roughly 400 and 700 nanometers. Dividing this 300 nanometer band into, for example, 30 sub-bands of 10 nanometers provides significantly more information on the color than an instrument that uses three color filters to determine the color.

Many spectrometers are commercially available, and many of them have spectral resolution of less than 10 nanometers, so they are well suited for this task. Common forms of spectrometers comprise an entrance slit, a collimating mirror, a grating, a "camera" (refocusing) mirror and a detector. An early example of such a spectrometer is U.S. Pat. No. 3,414,355, the disclosure of which is hereby incorporated by reference in its entirety.

The driving considerations for the spectrometer in the preferred embodiment of the present invention comprise small size, low cost and durability. One spectrometer that satisfies these considerations is the USB2000+™ spectrometer from Ocean Optics Inc., Dunedin, Fla. This spectrometer provides output of the measurement via a USB port, so the data can be analyzed by a computer with appropriate software. Other commercially available or custom built spectrometers may also comprise various embodiments of the present invention.

Because a spectrometer provides an electrical signal that is proportional to the amount of light in each wavelength band, it is possible to provide users with several pieces of useful information. Three desirable results are the spectral coefficients of retroreflection, the retroreflected chromaticity coordinates and the coefficient of retroreflection. The first of these is defined as the ratio of the retroreflected light in each wavelength band to the output of the source 101 in that same band. Because white retroreflectors must reflect approximately equally at all wavelengths (this is the definition of white) the instrument can be calibrated with a white retroreflector and then spectral coefficients of retroreflection of any other material can be measured. To obtain the retroreflected chromaticity coordinates of the retroreflected light, the spectral coefficients of retroreflection can be integrated as described in ASTM E 811 Section 6.1 and then the coordinates calculated as described in Section 6.2. Finally, the coefficient of retroreflection can be computed by performing a weighted average of the spectral coefficients of retroreflection, with the weights being chosen to mimic the photopic response of the eye.

Use of a spectrometer as a receiver not only removes the constraint on the correlated color temperature of the lamp as ASTM E 811 teaches, it also makes it possible to use an LED light source, without regard to their spectral variability. It can do this because the variability of an LED within a single instrument can be held within acceptable limits for a spectrometer. Given this freedom, one can consider the low power usage and long life of LED's. These attributes make LED's a preferred light source for an instrument that includes a spectrometer. One may also use an incandescent lamp or other type of light source with a spectrometer as a receiver.

Figure 6:
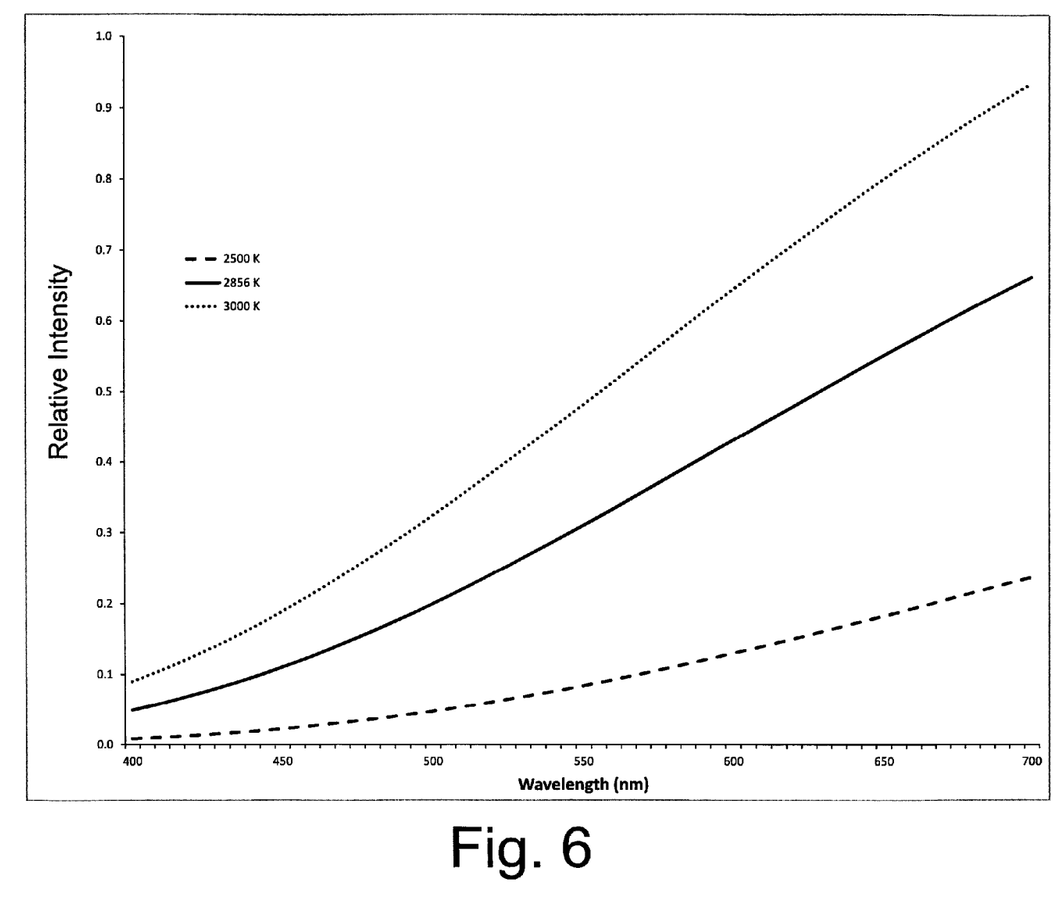
FIG. 6. is a plot of the visible spectrum of an incandescent lamp at three different color temperatures.

FIG. 6 plots the visible spectrum of an incandescent lamp at three different color temperatures, 2500K, 2856K and 3000K. At the lowest color temperature, the spectrum is fairly flat, but increases monotonically as the wavelength increases from 400 to 700 nm. The curve for the highest color temperature, 3000K, is similar, but the slope is much steeper. In the middle is the curve for 2856K, which corresponds to the CIE Standard Source A. It also is a gently sloped curve with a monotonic increase with wavelength over the visible spectrum. This characteristic smoothness, along with similarity of curves of different color temperatures, enables the use of tristimulus filters to measure color. It is difficult to make tristimulus filters that convert the wavelength response of a typical silicon detector into something approximating one of the tristimulus functions; to do so with sufficient accuracy to deal with rapidly varying spectra is impractical. This is why ASTM standard E 811 specifies an incandescent lamp.

Figure 7:
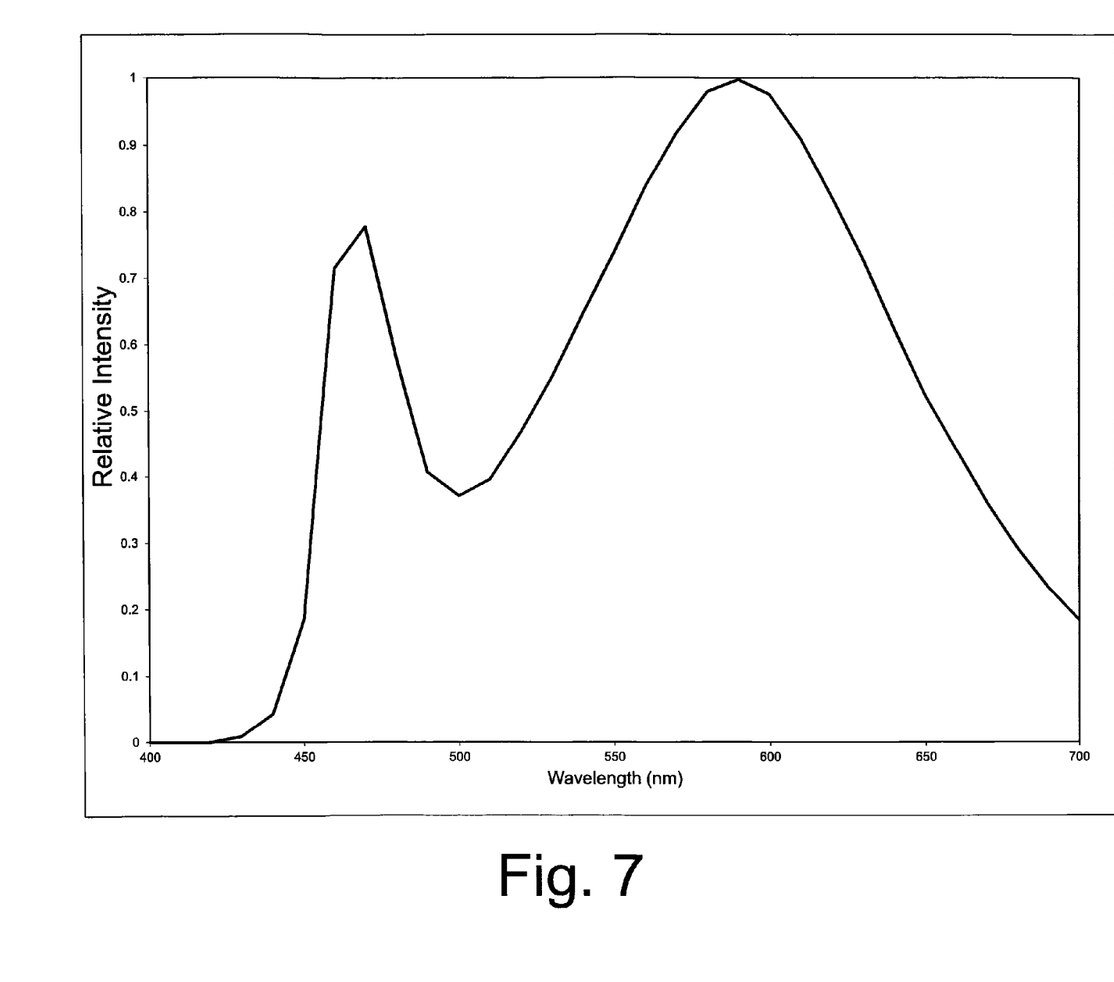
FIG. 7. is a plot of the visible spectrum of a light emitting diode (LED).

FIG. 7 plots the spectrum of a typical white LED, in this case a Nichia NSPL500DS-E, available from Nichia America Corporation, Torrance, Calif. It consists of a blue LED, with a peak emission wavelength near 460 nm, coated with a phosphor that emits a broader peak in the region of 590 nm. Although this spectrum is typical, the peak emission wavelength of the LED can easily vary by 10 nm due to manufacturing variation and temperature, and the ratio of the heights of the two peaks can vary substantially for the aforementioned reasons and as the electric current driving the LED changes. Clearly, the spectrum from a white LED has steeper slopes and more variability than an incandescent lamp. For the illustrated reasons, various preferred embodiments of the present invention comprise a spectrometer in conjunction with the LED light source.

The skilled artisan will recognize that the spectral retroreflectometer embodiments described herein provide an improved instrument for measuring the retroreflectance of materials in a way that yields several pieces of useful information.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification. Thus, while the above description contains many specificities, these should not be construed as limitations on the scope, but rather as an exemplification of one preferred embodiment thereof. For example, although the first, or illumination, optical path has been described as being reflected by the beamsplitter and the second, or retroreflection, path as transmitted, the first and second paths may be interchanged. An instrument based on a transmitted illumination path and reflected retroreflection path may have some advantages with regard to shape, size, scattered light and so forth.

What is claimed is:

1. An apparatus for measuring retroreflectivity of materials, comprising: an LED light source; a spectrometer; a first optical path configured to direct an illumination beam from the LED light source to illuminate with collimated light, a material to be tested; and a second optical path to direct a retroreflected beam from the material to the spectrometer, wherein the illumination optical path further comprises an annular aperture to collect the illumination beam, and wherein the second optical path comprises: a focusing lens to collect the retroreflected beam from the material to be tested; a beamsplitter to reflect a portion of the collected retroreflected beam and to transmit the portion of the collected retroreflected beam that is not reflected by the beamsplitter; a receiver aperture to collect the transmitted portion of the beam; and an optical fiber to transfer the light from the receiver aperture to the spectrometer.

2. An apparatus as described in claim 1 in which the illumination optical path further comprises a beamsplitter to transmit a portion of the collected illumination beam and to reflect the portion of the collected illumination beam that is not transmitted by the beamsplitter.

3. An apparatus as described in claim 1 in which the first optical path further comprises a lens that collects the illumination beam from the LED light source into an aperture, a beamsplitter and a collimating lens.

4. An apparatus as described in claim 1, wherein the spectrometer comprises grating and associated photodetectors.

5. An apparatus for measuring retroreflectivity of materials, comprising: an LED light source; a spectrometer; a first optical path configured to direct an illumination beam from the LED light source to illuminate with collimated light, a material to be tested, the first optical path comprising: a lens that collects the illumination beam from the light source, an annular aperture to collect the illumination beam from the lens, and a beamsplitter that transmits a portion of the illumination beam collected from the lens and reflects the portion of the illumination beam not transmitted through the beamsplitter to the material to be tested; a second optical path to direct a retroreflected beam from the material to be tested to the spectrometer, the second optical path comprising: a focusing lens to collect the retroreflected beam retroreflected from the material to be tested, the beamsplitter that transmits a portion of the retroreflected beam collected from the focusing lens and reflects the retroreflected beam portion that is not transmitted through the beamsplitter, a spectrometer aperture that collects the portion of the retroreflected beam transmitted by the beamsplitter, and an optical fiber to transfer the retroreflected beam collected by the spectrometer aperture, from the spectrometer aperture to the spectrometer.

6. An apparatus for measuring retroreflectivity of materials, comprising: an LED light source; a spectrometer; a first optical path configured to direct an illumination beam from the LED light source to illuminate with collimated light, a material to be tested; and a second optical path to direct a retroreflected beam from the material to the spectrometer, wherein the illumination optical path further comprises an annular aperture to collect the illumination beam, and wherein the second optical path comprises: a focusing lens to collect the retroreflected beam from the material to be tested; a beamsplitter to reflect a portion of the collected retroreflected beam and to transmit the portion of the collected retroreflected beam that is not reflected by the beamsplitter; a receiver aperture to collect the transmitted portion of the beam; and a lens to transfer the light from the receiver aperture to the spectrometer.

* * * * *